United States Patent [19]

Allen et al.

[11] Patent Number: 4,829,604
[45] Date of Patent: May 16, 1989

[54] WRIST SUPPORT DEVICE AND METHOD OF FABRICATING SAME

[75] Inventors: Francis Allen, Lincoln, Nebr.; James A. Creasey, Boulder; Ronald Brant, Greeley, both of Colo.

[73] Assignee: VIM Corporation, Boulder, Colo.

[21] Appl. No.: 150,041

[22] Filed: Jan. 29, 1988

[51] Int. Cl.⁴ ................. A41D 19/00; A41D 13/08
[52] U.S. Cl. ......................................... 2/170; 2/162
[58] Field of Search .................. 2/24, 20, 162, 170, 2/338, 167

[56] References Cited

U.S. PATENT DOCUMENTS

| | | | |
|---|---|---|---|
| 856,282 | 6/1907 | Moss | 2/170 |
| 3,786,804 | 1/1974 | Lewis | 2/24 |
| 4,120,052 | 10/1978 | Butler | 2/24 |
| 4,183,098 | 1/1980 | Knowles, Jr. | 2/162 |
| 4,193,135 | 3/1980 | Rhee | 2/162 |
| 4,273,130 | 6/1981 | Simpson | 2/338 |
| 4,462,116 | 7/1984 | Sanzone et al. | 2/170 |
| 4,531,241 | 7/1985 | Berger | 2/162 |

FOREIGN PATENT DOCUMENTS

| | | | |
|---|---|---|---|
| 730310 | 9/1932 | France | 2/170 |
| 597852 | 4/1978 | Switzerland | 2/170 |

Primary Examiner—Werner H. Schroeder
Assistant Examiner—Jeanette E. Chapman
Attorney, Agent, or Firm—John E. Reilly

[57] ABSTRACT

A support device for a wrist or forearm is made up of a band having an outer cushion layer, intermediate support layer and inner cushion layer bonded together, and a flexible strap is attached at one end to the outer surface of said band and has a free end which is looped through a buckle at the attached end of the band and reversed upon itself with a VELCRO ® type fastener between the free end and a portion of the strap to adjustably secure the support device around the wrist or forearm.

8 Claims, 1 Drawing Sheet

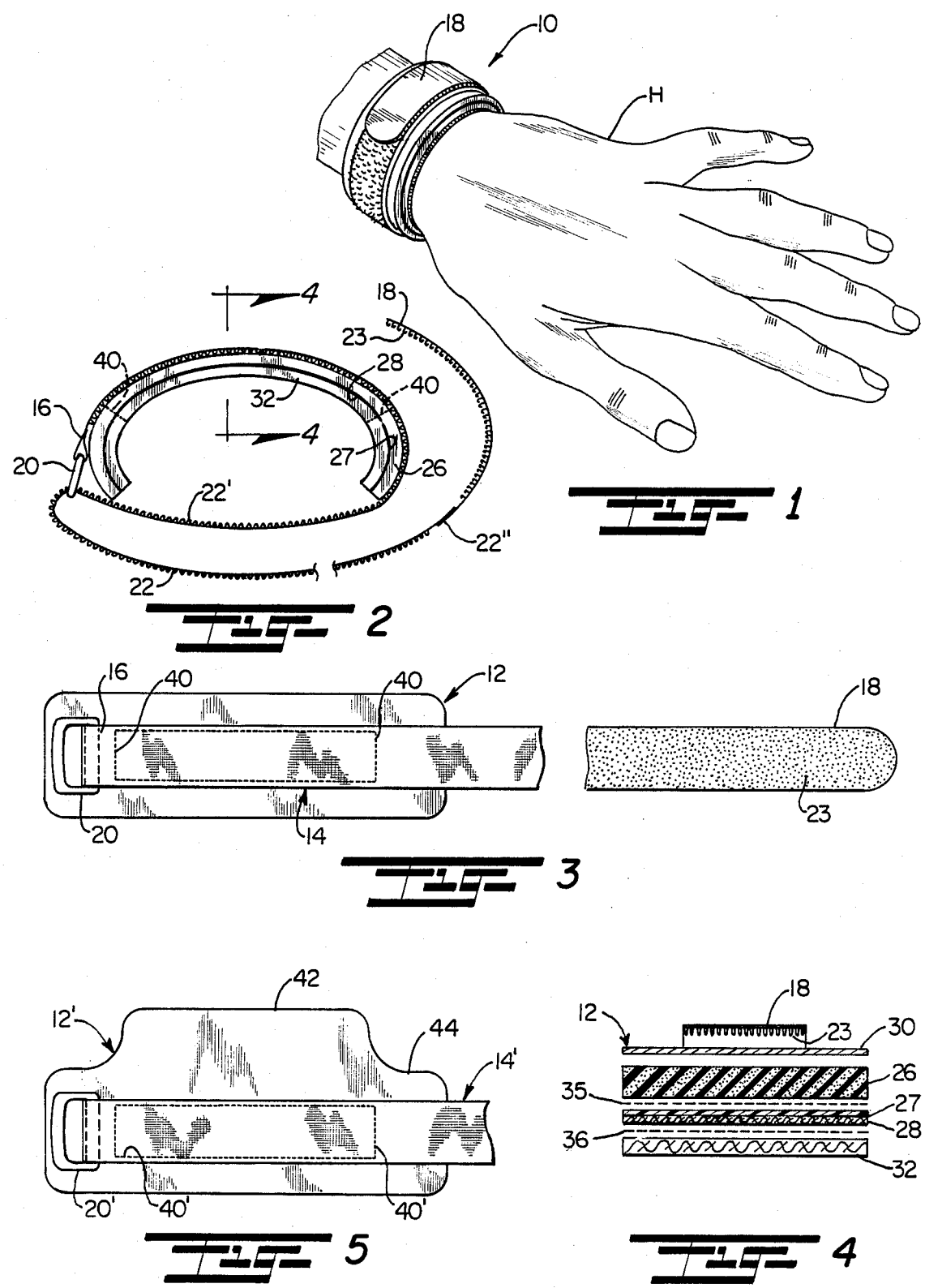

WRIST SUPPORT DEVICE AND METHOD OF FABRICATING SAME

This invention relates to exercise or athletic apparel; and, more particularly relates to a novel and improved wrist support device and method of making same, the device having particular utility in supporting the wrist and forearm during athletic activities.

BACKGROUND AND FIELD OF THE INVENTION

Many sports and exercise activities place considerable stress on the wrists. For example, certain gymnastic exercises require that the wrists and arms support the weight of the body and absorb the acceleration and deceleration forces of the body in a multitude of positions. Certain exercises or routines in weight-lifting also subject the wrists and arms to extreme stress or strain, particularly in a direction tending to bend the hands backwards about the wrists. In these and other activities, the wrists are vulnerable to tendon, ligament and soft tissue injuries which may result from excessive bending or turning of the hands, wrists and arms in directions beyond their physiological limits.

In the past, attempts have been made to protect the wrists from undue stress in various athletic endeavors. With varying degrees of success, wrist movement has been restricted by the use of tape or by rigid splints or pads immovably secured or placed around the area to be protected. These approaches, while marginally effective, tend to be cumbersome, bulky and flimsy, and therefore unsuitable for the user who requires considerable freedom of movement of the wrists but at the same time supporting the wrists against undesirable forces or strain. When the wrists are taped, the tension applied is limited since it tends to cut off blood circulation. In addition, other devices presently in use do not afford sufficient support for that area of the wrists ahead of the carpal bone structure and along the back of the hand while affording the maximum degree of comfort and flexibility or freedom of movement to the user.

SUMMARY OF THE INVENTION

It is therefore an object of the present invention to provide for a novel and improved wrist support device and method of making same.

It is another object of the present invention to provide for a novel and improved wrist support for the human wrist which can be adjusted but snugly secured in the desired position on the wrist so as to minimize application of undue strain and, once secured, will further minimize any inadvertent slipping or movement of the wrist support with respect to the wrist.

A further object of the present invention is to provide for novel and improved exercise apparel adapted for adjustable but secure attachment to the wrists or forearms without significant restriction in mobility; and further to provide directional support and mobility to the wrist while affording maximum comfort, containing body heat within the apparel and permit any desired increase or decrease in pressure and/or support to the area where applied.

A further object of the present invention is to provide a wrist support capable of protecting the wrist against injury and specifically is capable of achieving flexible support of the carpal bones of the wrist which are anchored at the distal ends of the radius and the ulna bones in the forearm without detrimentally affecting blood circulation.

In accordance with the present invention, there has been devised exercise apparel for the human wrist or forearm which is broadly comprised of a generally rectangular band of a length to circumscribe a substantial circumferential portion of the wrist or forearm and of a width substantially less than its length, the band having an outer cushion layer composed of a flexible, compressible material, a support layer bonded to the outer layer and composed of a flexible but inelastic material, the support layer resisting forces applied parallel to the width of the band. An inelastic but flexible strap is superimposed on the band and has one end securely attached thereto, the strap extending in a direction parallel to the length of the band and being of a length to completely encircle the band and wrist or forearm of the wearer, the strap having a width substantially less than the width of the band and terminating in a free end opposite to its attached end; and adjustable fastening means are operative to releasably fasten the free end to the attached end in encircled relation to the band so as to retain the band on the wrist or forearm of the wearer. Preferably, an inner cushion layer extends the length and width of the band add is bonded to an inner surface of the support layer, the outer surface of the support layer bonded to the outer layer. Further, the attached end of the strap is secured to the external surface of the outer layer by stitching across a portion or portions of the band, and the stitching unites the strap to the band in such way as to avoid bunching or folding of the band when it is securely tightened onto the wrist or forearm.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a somewhat perspective view of a preferred form of wrist support device in attached relation to the wrist;

FIG. 2 is an enlarged end view of the preferred form of wrist support device shown in FIG. 1;

FIG. 3 is a top plan view of the preferred form of wrist support device in accordance with the present invention;

FIG. 4 is an enlarged cross-sectional view taken about lines 4—4 of FIG. 2; and

FIG. 5 is a somewhat fragmentary top plan view of a modified form of wrist support device in accordance with the present invention.

DETAILED DESCRIPTION OF THE PREFERRED EMBODIMENT

Referring in more detail to the drawings, there is illustrated in FIGS. 1 to 4 a preferred form of support device 10 for the wrist or forearm which is specifically adapted for use in athletic or exercise activities, such as, gymnastics, weight-lifting, bowling, golf or tennis. As illustrated in FIG. 1, the principal intended application for the wrist support is to be placed over but slightly in front of the wrist joint and, in particular, forwardly of the carpal bone area and toward the back of the hand designated at H. This is given more for the purpose of illustration and not limitation, it being apparent from the following description that the support device may be snugly secured in different locations on the wrist as well as on the forearm of the user, if desired.

The preferred form of wrist support device 10 is broadly comprised of a generally rectangular band 12 which is of a length sufficient to circumscribe the greater circumferential extent of the human wrist and is of a width substantially less than its length. A flexible strap 14 is superimposed on the band and has one end portion 16 which is attached to the band and a free end 18 opposite to the attached end. The strap extends in a direction parallel to the length of the band and is of a total length to encircle the band and wrist at least once when applied to the wrist of the wearer, the width of the strap 14 being substantially less than the width of the band 12. Preferably, the attached end 16 of the strap includes a buckle or fastening loop 20 so that the free end 18 of the strap can be passed through the buckle, then returned or reversed in direction upon itself, as illustrated in FIG. 2. Adjustable fastening means preferably take the form of a first fastener portion 22 defined by loops applied along one surface of the attached end 16 of the strap and a second or complementary fastener portion 23 defined by interlocking hooks extending along a facing surface of the free end 18 of the strap. Briefly, once the strap is tightened around the wrist to the desired degree, the hooks 23 on the loose end may be brought into engagement with the loops 22 in order to securely but releasably fasten the loose end to the desired degree of tautness, as illustrated in FIG. 1.

Considering now the detailed construction and arrangement of the preferred form of band 12, as noted from FIG. 4, the band is made up of an outer cushion layer 26, an intermediate layer or layers 27 and 28, and an inner cushion layer 32. An external, relatively thin cloth layer 30 may be applied to the external surface of the cushion layer 26, the cloth layer 30 being suitably composed of Lycra, ballastic nylon, cotton or closed loop tricot material. The outer cushion layer 26 is preferably several times the thickness of the cloth layer and is composed of a foam rubber material, such as, a 5 lb. to 7 lb. per cubic foot density neoprene foam. Other rubber or rubber-like materials, such as, natural or synthetic rubber foam or plastic foam materials may be employed in the makeup of the support layer 26, this layer having little strength but excellent compressibility so as to offer maximum comfort to the wearer. The layer 27 is a high strength, relatively thin layer which is flexible so as to conform to the major wrist bone but yet resist any stretching or collapsing of the band particularly in a direction across the width of the band. A preferred material employed in the composition of the layer 27 is a low density polyethylene which is employed alone or combined with a high strength layer 28 which is preferably composed of a scrim or a reinforced woven fabric material.

Finally, the inner surface layer 32 which is applied to the inner surface of the layer 28 is preferably composed of fleeced dacron or terry cloth which possesses at least limited moisture absorbing or wicking capacity. Both the external layer 30 and internal layer 32 may be united to the layers 26 and 28, respectively, by bonding or heat sealing. As represented in FIG. 4, the intermediate layers 27 and 28 are united by a pressure-sensitive adhesive material or bonding agent. Another pressure-sensitive adhesive layer 35 serves to unite the intermediate layer 27 to the inner surface of the cushion layer 26, and a pressure-sensitive adhesive layer 36 unites the layer 28 to the outer surface of the inner cushion layer 32.

In the preferred construction of the strap 14, the loop portion 22 extends continuously along the inner surface of the strap, the inner surface being an extension of that portion designated at 22' in facing relation to the wrist and extends continually to a location, designated at 22", which is the juncture with the free end portion 18. The hook portion 23 extends continuously from the juncture 22' to the extremity of the free end 18 along that surface which is on a side opposite to the inner loop portion designated at 22. Thus, while the surface 22 would be in facing relation to the wrist as at 22', once doubled upon itself in passing through the buckle or loop 20, the surface 22 becomes the external surface of the strap, and the hook portion 23 extends along the inner surface and for a sufficient length to extend around the entire length or periphery of the band beyond the buckle 26 so as to attach itself to the surface 22 beyond the buckle 20. The loop portion 22 has excellent moisture-absorbent properties and, for example, one form of fastener is that sold under the trademark VELCRO ®.

Another feature of the present invention resides in the attachment of the strap to the band by transverse stitching 40 and lengthwise stitching 44 so as to form a generally rectangular pattern. As best seen from FIG. 4, the cross-stitching 40 extends through the entire thickness of the band 12. As shown, the strap 14 is stitched centrally along the length of the band, and in stitching the strap to the band a slight gather or looseness is provided in the strap so that the strap will lay flat along the external surface of the band when it is curved around the wrist or forearm portion. In the completed assembly, the intermediate layers 27 and 28 effectively form a single layer which will serve to stiffen and strengthen the entire band. The stitching as described not only distributes the attachment points but, by virtue of extending along the external surface of the length of the band, has been found to resist any tendency to crease or bunch up the material of the band. In this relation, the high strength intermediate layer 27 cooperates in resisting any tendency to fold or gather when the band is snugly secured around the wrist.

A modified form of wrist support is illustrated in FIG. 5 wherein like parts are enumerated with prime numerals corresponding to those of the preferred form. In the modified form, the band 12' has a strap 14' secured in the same manner as described with respect to FIGS. 1 to 4.

However, the band 12' has a lateral extension 42 projecting from one side edge 44 of the band. It will be evident that the entire length of the band may be increased in width, although it is preferred to increase the width along an intermediate section as defined by the lateral extension 42 of the band 12' for a distance sufficient to overlie the back of the hand H, and opposite ends of the band 12' of reduced width may then more freely curve or bend around the wrist.

The wider wrist band or support 12' as illustrated in FIG. 5, is of particular utility in immobilizing the wrist joint in sports, such as, bowling, football and golf. Also, it has excellent properties which lend itself well to act as a brace in protecting an injured hand or wrist. Typically, the band of the modified form may be on the order of 3" to 4" wide and having a length on the order of 6.8". Of course, on wider bands, it may be desirable to employ a pair of straps extending lengthwise in spaced, parallel and juxtaposed relation to one another along the band. In the preferred form of band as described with reference to FIGS. 1 to 4, the width is more on the order of 2″ and of a length which is on the order of 6.8″. The wrist support may be modified in construction by eliminating one of the intermediate layers 27 and 28. For example, the scrim layer 28 may be eliminated and the stitching 40 is passed through the inner layer 32 to lend the necessary strength and non-elasticity to the band as well as to resist bending or folding of the band in the direction of its width.

In certain exercises or activities such as, gymnastic exercises the wrist support or brace would be applied as described to extend over the transverse carpal ligament with the free ends of the band disposed on the inside of the wrist, as illustrated in FIG. 1. In weight-lifting it may be more desirable to place the wrist support behind the wrist joint and over the forearm with the free ends of the band placed over or meeting one another on the outer surface of the forearm, or in other words, reversed 180° from that illustrated in FIG. 1. In this way, the band will serve as more of a protective device against certain of the tendons along the inner part of the wrist and forearm area. Similarly, the device 10 may be employed at other points along the forearm closer to the elbow to serve as a means of relief against tendonitis, such as, often encountered in playing the game of tennis.

It is therefore to be understood that various modifications and changes may be made in the method and resultant preferred and alternate forms of articles of manufacture of the present invention without departing from the spirit and scope thereof as defined by the appended claims.

I claim:

1. A support band for the wrist or forearm comprising:
   a generally rectangular band of a length to circumscribe a substantial circumferential portion of the human wrist or forearm and of a width substantially less than said length, said band having an outer cushion layer composed of a flexible, compressible material, a support layer bonded to said outer layer and composed of a flexible but inelastic material, said support layer resisting forces applied parallel to the width of said band;
   an inelastic but flexible strap superimposed on said band and having one end attached thereto, said strap extending in a direction parallel to the length of said band and of a total length to encircle said band and said wrist or forearm at least once when applied to the wrist or forearm of the wearer, said strap having a width substantially less than the width of said band and terminating in a free end opposite to said attached end; and
   adjustable fastening means to releasably fasten said free end to a portion of said attached end in encircled relation to said band whereby to retain said band on the wrist or forearm of the wearer, said attached end including means securing said strap to said outer layer across said band, said securing means defined by stitching extending at least through said attached end, said outer cushion layer and said support layer.

2. A support band according to claim 1, wherein an inner layer extends the length and width of said band, said inner layer bonded to an inner surface of said support layer, and an outer surface of said support layer bonded to said outer layer.

3. A support band according to claim 1, wherein said outer layer is composed of a foam rubber or rubber-like material.

4. A support band according to claim 2, wherein said inner layer is composed of a moisture-absorbent material.

5. A support band according to claim 1, said adjustable fastening means located on confronting surface portions of said free end and said attached end, said fastening means comprising interlocking loop and hook portions.

6. A wrist support device comprising:
   a generally rectangular band of a length to circumscribe a substantial portion of the human wrist and of a width substantially less than said length;
   an outer thick cushion layer extending the width and length of said band, said outer layer composed of a foam rubber or rubberlike material;
   a thin intermediate support layer extending the width and length of said band, said support layer bonded to an inner surface of said outer layer and composed of flexible but inelastic, high strength material, said support layer resisting bending in response to forces applied parallel to the width of said band;
   an inner cushion layer extending the length and width of said band, said inner cushion layer bonded to an inner surface of said intermediate support layer opposite the surface of said support layer to which said outer cushion layer is bonded, said inner cushion layer composed of a moisture-absorbent material;
   an inelastic but flexible strap superimposed on said outer cushion layer, said strap extending in a direction parallel to the length of said band and of a total length to encircle said band when applied to the wrist of a wearer, said strap terminating in a free end opposite to said attached end;
   said attached end having a loop through which said free end is inserted, said free end reversed upon itself in a circular direction opposite the direction in which said free end was inserted into said loop; and
   adjustable fastening means to releasably fasten said free end to a portion of said strap in outer concentric relation to said band.

7. A wrist support according to claim 6, including a cloth layer affixed to an outer surface of said outer cushion layer.

8. A wrist support according to claim 6, said intermediate support layer including a layer composed of a woven fabric material coated with a polyethylene material.

* * * * *